United States Patent
Tang et al.

(10) Patent No.: US 11,137,377 B1
(45) Date of Patent: Oct. 5, 2021

(54) DISPERSIVE SOLID-PHASE EXTRACTION MATERIAL, PREPARATION METHOD THEREFOR AND APPLICATION THEREOF

(71) Applicant: GUANGXI ZHUANG AUTONOMOUS REGION CENTER FOR DISEASE CONTROL AND PREVENTION, Guangxi (CN)

(72) Inventors: Yang Tang, Guangxi (CN); Yanhua Liao, Guangxi (CN); Ping Liu, Guangxi (CN); Ningsheng Lei, Guangxi (CN); Chuan Liang, Guangxi (CN)

(73) Assignee: GUANGXI ZHUANG AUTONOMOUS REGION CENTER FOR DISEASE CONTROL AND PREVENTION, Nanning (CN)

( * ) Notice: Subject to any disclaimer, the term of this patent is extended or adjusted under 35 U.S.C. 154(b) by 0 days.

(21) Appl. No.: 17/263,146

(22) PCT Filed: Jun. 25, 2019

(86) PCT No.: PCT/CN2019/092826
§ 371 (c)(1),
(2) Date: Jan. 25, 2021

(87) PCT Pub. No.: WO2020/215477
PCT Pub. Date: Oct. 29, 2020

(30) Foreign Application Priority Data

Apr. 22, 2019 (CN) .......................... 201910324127.1

(51) Int. Cl.
*G01N 30/06* (2006.01)
*G01N 30/02* (2006.01)

(52) U.S. Cl.
CPC ....... *G01N 30/06* (2013.01); *G01N 2030/027* (2013.01); *G01N 2030/062* (2013.01)

(58) Field of Classification Search
CPC ............. G01N 30/06; G01N 2030/062; G01N 2030/027
See application file for complete search history.

(56) References Cited

U.S. PATENT DOCUMENTS

2013/0302505 A1   11/2013   Nichols et al.

FOREIGN PATENT DOCUMENTS

| CN | 105153435 A | 12/2015 |
| CN | 108250452 A | 7/2018 |
| CN | 109307667 A | 2/2019 |

OTHER PUBLICATIONS

Zhou, Nengzhi et al. "Low-cost Humic acid-bonded silica as an effective solid-phase extraction sorbent for convenient determination of aflatoxins in edible oils," Analytics Chimica Acta, vol. 970, Mar. 29, 2017, pp. 40-41. (Year: 2017).*

(Continued)

*Primary Examiner* — Jennifer Wecker
*Assistant Examiner* — Michael Paul Shimek
(74) *Attorney, Agent, or Firm* — Dragon Sun Law Firm, PC; Jinggao Li, Esq.

(57) ABSTRACT

A dispersive solid-phase extraction material, a preparation method therefor and an application thereof. The method comprises: weighing humic acid and washing it using water under ultrasonic bath, centrifuging to obtain a solid precipitate; resuspending the solid precipitate in acetone, heating and evaporating until the acetone has evaporated completely to then obtain a residue; taking and placing the residue in a Soxhlet extractor, and adding a cleaning solution; cleaning by heating and refluxing until the refluxed liquid is clear and colorless, and then heating is stopped; taking out the cleaned material; drying the material at 100° C. for 1.5-2.5 h, cooling for 0.5-1 h, and sieving through a 120 mesh sieve; collecting the material under the sieve to obtain the dispersive solid-phase extraction material. The dispersive solid-phase extrac- (Continued)

Figure 1:
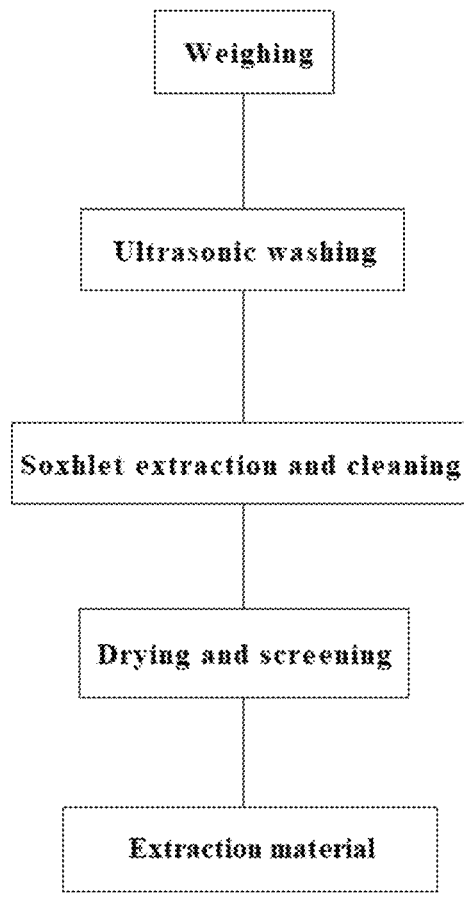
Figure 2:
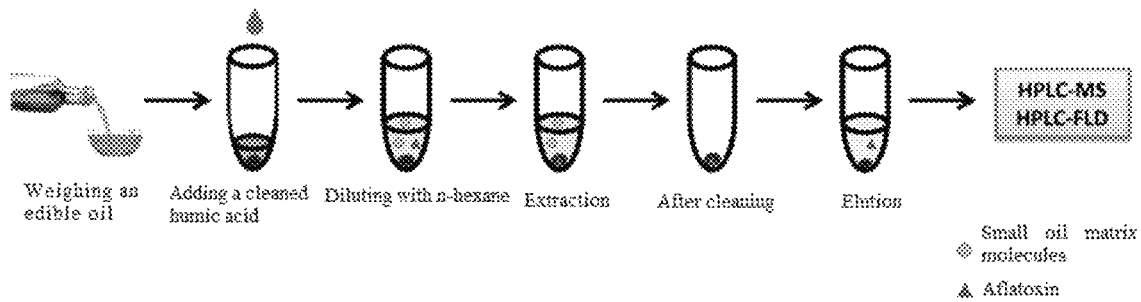

tion material can simultaneously extract and purify aflatoxins in edible oils for their detection.

6 Claims, 4 Drawing Sheets

(56) References Cited

OTHER PUBLICATIONS

International Search Report of PCT/CN2019/077966.
Written Opinion of PCT/CN2019/077966.
Liu, Bo et al. (Progress in Fractionation and Purification of Humic Acids) (Modern Chemical Industry), vol. 31, Oct. 31, 2011 (Oct. 31, 2011), p. 19.
Zhou, Nengzhi et al. "Low-Cost Humic Acid-Bonded Silica as an Effective Solid-Phase Extraction Sorbent for Convenient Determination of Aflatoxins in Edible Oils" Analytica ChimicaActa, vol. 970, Mar. 29, 2017 (Mar. 29, 2017), pp. 40 and 41.

* cited by examiner

DISPERSIVE SOLID-PHASE EXTRACTION MATERIAL, PREPARATION METHOD THEREFOR AND APPLICATION THEREOF

CROSS-REFERENCE TO RELATED APPLICATIONS

This Application is a national stage application of PCT/CN2019/092826. This application claims priorities from PCT Application No. PCT/CN2019/092826, filed Jun. 11, 2019, and from the Chinese patent application 201910324127.1 filed Apr. 22, 2019, the content of which is incorporated herein in the entirety by reference.

TECHNICAL FIELD

The present invention belongs to the technical field of detection of aflatoxins in edible oils, and particularly relates to a dispersive solid-phase extraction material, and a preparation method and application thereof.

BACKGROUND

China is not only a major edible oil producer, but also the largest edible oil consumer in the world, and average annual consumption of edible oils in China is increasing year by year with the continuous improvement of living standards. Therefore, as an important part of "food safety", "edible oil safety" is not only related to national health, but also directly affects the development of national economy.

Aflatoxins (AFs) are a major contaminant of edible oils and are secondary metabolites of *Aspergillus flavus* and *Aspergillus parasiticus*. Up to now, a total of 18 AFs has been reported, among which $AFB_1$, $AFB_2$, $AFG_1$ and $AFG_2$ are the four most common AFs. The AFs have the characteristics of high toxicity, high carcinogenicity, high mutagenicity and high teratogenicity and thus are extremely harmful to human health. Among the AFs, Al—Bi is most toxic and its toxicity is much higher than that of cyanide, arsenide and organic pesticides. Moreover, $APB_1$ is also the most powerful natural carcinogen reported so far. In warm and humid areas, foods may become damp and moldy during growth, harvesting, storage and processing and consequently have a high probability of being contaminated by the AFs. The foods susceptible to contamination by the AFs mainly include oil crops such as peanuts, maize and soybeans, and processed foods such as edible oils, dried pulp and seasonings. Ingestion of the edible oils contaminated by the AFs not only harms national health but also results in significant economic loss. Therefore, it is of great significance to accurately determine the content of the AFs in the edible oils.

At present, methods for detecting the AFs in the edible oils mainly include liquid chromatograph-mass spectrometry (LC-MS) and liquid chromatograph-fluorescence detection (LC-FLD). The edible oils are a sample with a very complex matrix, contain more than 95% of triglyceride compounds, and also contain 1%-5% of fatty acids, vitamins, fat-soluble pigments and other esters. However, the AFs in the contaminated edible oils is generally at a trace level of ng/kg, and a large number of triglyceride compounds in the edible oils will cause serious interference on detection. Hence, before a trace amount of aflatoxins in the edible oils is detected, it is necessary to perform sample pretreatment, and eliminate interference from the oil matrix while the AFs are extracted.

A sample pretreatment method is the core of the detection of the AFs in the edible oils, and decides the efficiency and cost of the entire detection method. At present, in the detection of the AFs in the edible oils, immunoaffinity columns (IAC) or multifunctional columns (MFC) are commonly used to process samples. However, these sample pretreatment methods will face the following several problems when being used for detecting the AFs in the edible oils in large quantities: 1. liquid-liquid extraction consumes a large number of organic reagents and has a great influence on recovery rates of the methods; 2. the separation of an extraction step and a purification step makes an operation process cumbersome and time- and labor-consuming; and 3. IAC and MFC columns used in sample pretreatment are expensive. Based on this, at present, the food safety detection industry faces problems such as too cumbersome operation of sample pretreatment methods, high detection cost, and poor stability when detecting the AFs in the edible oils in large quantities. In order to assess, monitor and ensure the safety of the edible oils, the AFs in local edible oils are detected in large quantities every year across the country, but the use of the above sample pretreatment methods will undoubtedly consume a lot of time and manpower as well as huge expenses. If a reliable detection method can be established, which is easy and simple to operate and can significantly reduce the detection cost, this unnecessary consumption can be avoided to a large extent and thus lots of social resources can be saved. Therefore, in order to solve the problems faced by the edible oil detection industry, there is an urgent need to develop a simple, cheap, and reliable novel detection method for detecting a trace amount of AFs in edible oils in large quantities.

SUMMARY

For solving the above technical problems, the present invention provides a dispersive solid-phase extraction material, and a preparation method and application thereof. The dispersive solid-phase extraction material is applicable to the field of detection of AFs in various edible oils and has the effects of high simplicity and convenience in processing, low cost, small matrix interference, high sample recovery rate and the like.

The technical solutions of the present invention for solving the above technical problems are as follows. A preparation method of a dispersive solid-phase extraction material is provided. The method includes the following steps:

S1. weighing a humic acid, performing ultrasonic washing for 12-18 min, performing centrifugation after washing to obtain a solid precipitate, resuspending the solid precipitate in acetone, and performing heating for evaporation until the acetone is completely evaporated to obtain a residue;

S2. placing the residue obtained in step S1 in a Soxhlet extractor, adding 180 mL of cleaning liquid, performing heating reflux for cleaning until a refluxed liquid is clear and colorless, and stopping heating; and S3. taking out the material cleaned in step S2, drying the material at 100° C. for 1.5-2.5 h, cooling the dried material for 0.5-1 h, then screening the cooled material through a 120-mesh sieve, and obtaining a substance under the sieve, i.e., the dispersive solid-phase extraction material.

The preparation method according to the present invention has the following beneficial effects. The preparation method of the dispersive solid-phase extraction material is applicable to a variety of commercial humic acids at home and abroad, has a simple process and is easy to control. The humic acid prepared after cleaning has stable properties and can be used to simultaneously extract and purify aflatoxins in various edible oils for their detection. Therefore, the quality of the edible oils is ensured.

Based on the above technical solution, the following improvement can further be made on the present invention.

Further, in the step S1, after ultrasonic washing, incubation is performed at room temperature for 6-10 h, a supernatant is removed, the operation of ultrasonic washing and incubation is cyclically repeated for 10 times, and then centrifugation is performed to obtain the solid precipitate.

The beneficial effects of adopting the above further solution are as follows. Effective constituents in the material can remain sufficiently after incubation at room temperature. Moreover, the repetition of the operation for 10 times facilitates removing fulvic acid and some other water-soluble impurities in the humic acid.

Further, heating the Soxhlet extractor in the step S2 includes heating the Soxhlet extractor in a water bath, wherein a water bath temperature is 70-90° C., and the heating reflux time is 8-30 h.

The beneficial effect of adopting the above further solution is as follows. The cleaning effect is excellent by evaporating and refluxing the cleaning liquid and making the cleaning liquid come into contact with the humic acid for many times.

Further, in the step S2, the residue which is subjected to heating reflux for 20 h is taken out, air-dried naturally, ground and then placed in another Soxhlet extractor; 180 mL of cleaning liquid is then added, heating is performed again for cleaning for 8-12 h until the refluxed liquid is clear and colorless, and heating is stopped.

The beneficial effect of adopting the above further solution is as follows. For some humic acids with more ulmic acid and alcohol-soluble impurities, the cleaning efficiency can be improved.

Further, the cleaning liquid for heating reflux for cleaning in the step S2 includes acetone, methanol, acetonitrile and water in a volume ratio of 6-8:4-6:6-8:1-2.

The beneficial effects of adopting the above further solution are as follows. The ulmic acid in the humic acids can be removed through the cleaning liquid and ineffective ingredients can be removed, thereby avoiding interference during subsequent detection.

The present invention further provides a dispersive solid-phase extraction material prepared through the above preparation method.

The dispersive solid-phase extraction material according to the present invention has the following beneficial effects. The dispersive solid-phase extraction material can be used to simultaneously extract and purify aflatoxins in edible oils for their detection. Therefore, the quality of the edible oils is ensured.

The present invention further provides an application of the above dispersive solid-phase extraction material in detection of aflatoxins in an edible oil.

The present invention further provides a method for detecting aflatoxins in an edible oil. The method includes sample pretreatment: weighing and mixing 1 g of edible oil sample and 50 mg of dispersive solid-phase extraction material as claimed in claim 6, adding 5 mL of n-hexane, performing shaking and centrifugation and removing a supernatant; and then adding 4 mL of eluent, performing shaking and centrifugation, taking a supernatant, drying the supernatant to obtain a sample to be measured, dissolving the sample to be measured and measuring the dissolved sample.

The sample pretreatment method according to the present invention has the following beneficial effects. The operation is simple and convenient. Compared with a classic immunoaffinity column, the sample pretreatment method can directly handle the oil sample without liquid-liquid extraction in advance and has a cost much lower than that of the classical method, which is only 1/20 of that of the classical method. The sample pretreatment method can handle a large number of samples at the same time and thus has the advantages of saving both time and labors. Moreover, the sample pretreatment method is suitable for purifying various edible oil matrixes, and has smaller matrix interference and relatively higher AFs recovery rate and thus a wide application prospect in the field of analysis of the AFs in the edible oils.

Further, the operation of adding n-hexane, performing shaking and centrifugation and removing the supernatant specifically includes two operations, wherein the first operation includes: adding 5 mL of n-hexane, performing shaking for 1.5-2 min, then performing centrifugation for 10-20 min at 9,000-12,000 r/min, and removing the supernatant; and the second operation includes: adding 5 mL of n-hexane, performing shaking for 20-40 s, then performing centrifugation for 5 min at 9,000-12,000 r/min, and removing the supernatant. In the operation of adding the eluent and performing shaking and centrifugation, the shaking is performed for 1.5-2 min and the centrifugation is then performed for 5 min at 9,000-12,000 r/min.

The beneficial effects of adopting the above further solution are as follows. By cleaning with the n-hexane for two times, it is more conducive to full removal of impurities in the oil sample, thereby avoiding interference of the oil matrixes on the detection.

Further, the eluent includes acetonitrile and water in a volume ratio of is 9:1.

The beneficial effect of adopting the above further solution is as follows. The AFs are eluted from the material through the eluent to achieve the extraction of the AFs in the edible oils for subsequent detection.

BRIEF DESCRIPTION OF THE DRAWINGS

FIG. 1 is a flowchart of a preparation method of a dispersive solid-phase extraction material according to the present invention;

FIG. 2 is a flowchart of a sample pretreatment method according to the present invention;

FIG. 3 is an LC-FLD chromatogram of Embodiment 1 of the present invention;

FIG. 4 is an LC-FLD chromatogram of Embodiment 5 of the present invention; and FIG. 5 is an LC-MS chromatogram of Embodiment 11 of the present invention.

DETAILED DESCRIPTION

The principle and features of the present invention are described below. The examples are given only for illustrating the present invention and are not intended to limit the scope of the present invention.

Embodiment 1

The present application provides a preparation method of a dispersive solid-phase extraction material. The preparation method includes the following steps.

In S1, 5 g of humic acid sample on sale in China is weighed and then put into a 1 L beaker; 500 mL of water is added and full stirring is performed for dispersion; the beaker is put into an ultrasonic bath for 15 min, incubation is performed at room temperature for 8 h after cleaning, and a supernatant is removed; 500 mL of water is added again, ultrasonic cleaning is performed for 15 min, incubation is performed at room temperature for 8 h, and a supernatant is removed; and the above steps are cyclically repeated for 10 times until there is no obvious light yellow in the supernatant under natural light by visual inspection. If the particles in the beaker are not completely precipitated after the sample incubating at room temperature for 8 h, the above steps are still cyclically repeated for 10 times for completing cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:6:6:1; the Soxhlet extractor is placed in a water bath and heated, wherein a water bath temperature is 82° C., and the heating reflux time is 30 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h, and the refluxed liquid in the extraction apparatus remains clear.

In S3, the material in the filtration paper cylinder cleaned in the step S2 is taken out; the cleaned material is dried at a drying temperature of 100° C. for 2 h; the dried material is put into the desiccator for cooling for 0.5 h and screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

Figure 3:
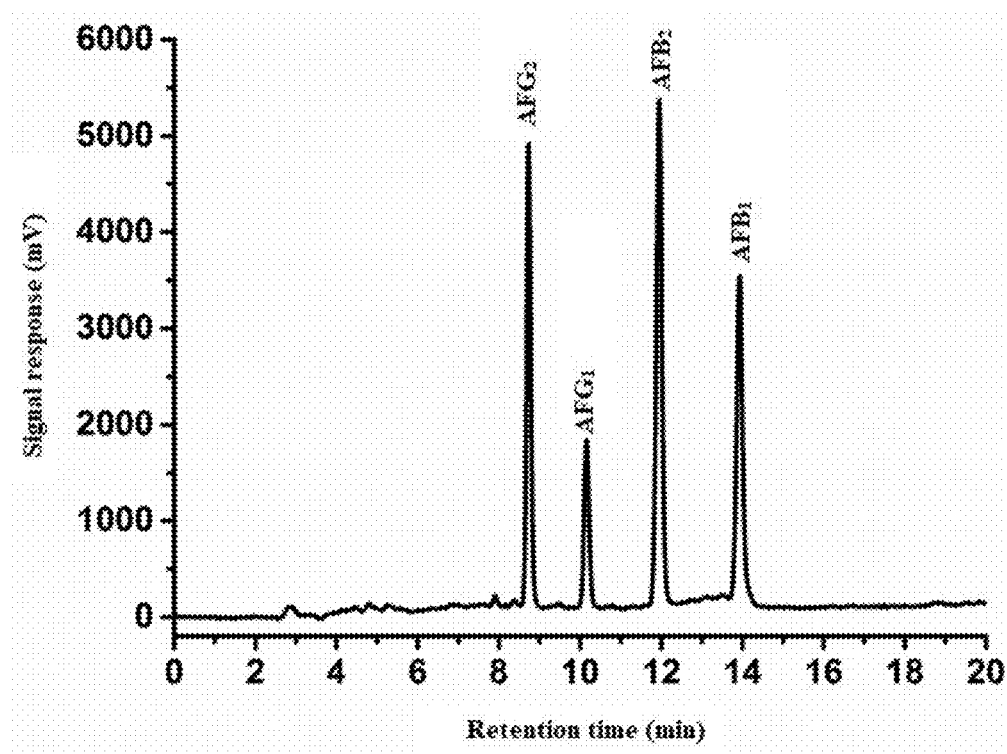

This embodiment provides a method for detecting an aflatoxin in an edible oil using the dispersive solid-phase extraction material prepared through the above preparation method. The method is particularly a sample pretreatment method and includes the following steps. 1 g of a blank blended oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 10 min at 9,000 r/min, and a supernatant is removed; and 5 mL of n-hexane is added again, the second shaking is performed for 30 s, the second centrifugation is performed for 5 min at 9,000 r/min, and a supernatant is removed; 4 mL of eluent is added, and shaking and centrifugation are performed, wherein the eluent includes acetonitrile and water in a volume ratio of 9:1, specifically, the shaking is performed for 1.5 min and the centrifugation is performed for 5 min at 9,000 r/min; all the supernatant is sucked out using a 5 mL syringe after the centrifugation ends; filtration is performed through a 0.22-μm microporous membrane, and the filtered material is transferred into a new centrifuge tube, and dried at 40° C. to obtain a sample to be measured, a solution including methanol and water which are mixed in a volume ratio of 1:1 is added to the sample to be measured to dissolve the sample, and the solution is analyzed through LC-MS or LC-FLD. A specific LC-FLD chromatogram is as shown in FIG. 3.

Embodiment 2

The present application provides a preparation method of a dispersive solid-phase extraction material. The preparation method includes the following steps.

In S1, 5 g of humic acid sample on sale in China is weighed and then put into a 1 L beaker; 500 mL of water is added and full stirring is performed for dispersion; the beaker is put into an ultrasonic bath for 12 min, incubation is performed at room temperature for 8 h after cleaning, and a supernatant is removed; 500 mL of water is added again, ultrasonic cleaning is performed for 12 min, incubation is performed at room temperature for 8 h, and a supernatant is removed; and the above steps are cyclically repeated for 10 times until there is no obvious light yellow in the supernatant under natural light by visual inspection. If particles in the beaker are not completely precipitated after the sample incubating at room temperature for 8 h in the sample incubation process, the above steps are still cyclically repeated for 10 times for cleaning; the cleaned sample and water together are transferred into a centrifuge tube for centrifugation for 6 min at 6,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:6:6:2; the Soxhlet extractor is placed in a water bath and heated, wherein a water bath temperature is 82° C., and the heating reflux for 30 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h, and the refluxed liquid in the extraction apparatus remains clear.

In S3, the material in the filtration paper cylinder cleaned in the step S2 is taken out; the cleaned material is dried at a drying temperature of 100° C. for 2 h; the dried material is put into the desiccator for cooling for 0.5 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

This embodiment provides a method for detecting an aflatoxin in an edible oil using the dispersive solid-phase extraction material prepared through the above preparation method. The method is particularly a sample pretreatment method and includes the following steps. 1 g of blank blended olive oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 10 min at 9,000 r/min, and a supernatant is removed; and 5 mL of n-hexane is added again, the second shaking is performed for 30 s, the second centrifugation is performed for 5 min at 9,000 r/min, and a supernatant is removed; 4 mL of eluent is added, and shaking and centrifugation are performed, wherein the eluent includes acetonitrile and water in a volume ratio of 9:1, specifically, the shaking is performed for 1.5 min and the centrifugation is performed for 5 min at 9,000 r/min; all the supernatant is sucked out using a 5 mL syringe after the centrifugation ends; filtration is performed through a 0.22-μm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD.

Embodiment 3

The present application provides a preparation method of a dispersive solid-phase extraction material. The preparation method includes the following steps.

In S1, 5 g of humic acid sample on sale in China is weighed and then put into a 1 L beaker; 500 mL of water is added and full stirring is performed for dispersion; the beaker is put into an ultrasonic bath for 16 min, incubation is performed at room temperature for 7 h after cleaning, and a supernatant is removed; 500 mL of water is added again, ultrasonic cleaning is performed for 16 min, incubation is performed at room temperature for 7 h, and a supernatant is removed; and the above steps are cyclically repeated for 10 times until there is no obvious light yellow in the supernatant under natural light by visual inspection. If particles in the beaker are not completely precipitated after the sample incubating at room temperature for 8 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 8:6:8:2; the Soxhlet extractor is placed in a water bath and heated, wherein a water bath temperature is 82° C., and the heating reflux is 20 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h, and the refluxed liquid in the extraction apparatus remains clear.

In S3, the material in the filtration paper cylinder cleaned in the step S2 is taken out; the cleaned material is dried at a drying temperature of 100° C. for 2.5 h; the dried material is put into the desiccator for cooling for 1 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

This embodiment provides a method for detecting an aflatoxin in an edible oil using the dispersive solid-phase extraction material prepared through the above preparation method. The method is particularly a sample pretreatment method and includes the following steps. 1 g of blank camellia oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 2 min, the first centrifugation is performed for 12 min at 10,000 r/min, and a supernatant is removed; and 5 mL of n-hexane is added again, the second shaking is performed for 30 s, the second centrifugation is performed for 5 min at 10,000 r/min, and a supernatant is removed; 4 mL of eluent is added, and shaking and centrifugation are performed, wherein the eluent includes acetonitrile and water in a volume ratio of 9:1, specifically, the shaking is performed for 2 min and the centrifugation is performed for 5 min at 11,000 r/min; all the supernatant is sucked out using a 5 mL syringe after the centrifugation ends; filtration is performed through a 0.22-μm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD.

Embodiment 4

The present application provides a preparation method of a dispersive solid-phase extraction material. The preparation method includes the following steps.

In S1, 5 g of humic acid sample on sale in China is weighed and then put into a 1 L beaker; 500 mL of water is added and full stirring is performed for dispersion; the beaker is put into an ultrasonic bath for 18 min, incubation is performed at room temperature for 10 h after cleaning, and a supernatant is removed; 500 mL of water is added again, ultrasonic cleaning is performed for 18 min, incubation is performed at room temperature for 10 h, and a supernatant is removed; and the above steps are cyclically repeated for 10 times until there is no obvious light yellow in the supernatant under natural light by visual inspection. If particles in the beaker are not completely precipitated after the sample incubating at room temperature for 10 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1.5 h, and then taken out; and then the residue is put into a desiccator for cooling for 30 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:4:6:1; the Soxhlet extractor is placed in a water bath and heated, wherein a water bath temperature is 82° C., and the heating reflux time is 28 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h, and the refluxed liquid in the extraction apparatus remains clear.

In S3, the material in the filtration paper cylinder cleaned in the step S2 is taken out; the cleaned material is dried at a drying temperature of 100° C. for 1.5 h; the dried material is put into the desiccator for cooling for 1 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

This embodiment provides a method for detecting an aflatoxin in an edible oil using the dispersive solid-phase extraction material prepared through the above preparation method. The method is particularly a sample pretreatment method and includes the following steps. 1 g of blank sunflower seed oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 10 min at 12,000 r/min, and a supernatant is removed; and 5 mL of n-hexane is added again, the second shaking is performed for 30 s, the second centrifugation is performed for 5 min at 12,000 r/min, and a supernatant is removed; 4 mL of eluent is added, and shaking and centrifugation are performed, wherein the eluent includes acetonitrile and water in a volume ratio of 9:1, specifically, the shaking is performed for 2 min and the centrifugation is performed for 5 min at 12,000 r/min; all the supernatant is sucked out using a 5 mL syringe after the centrifugation ends; filtration is performed through a 0.22-μm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD.

Embodiment 5

The present application provides a preparation method of a dispersive solid-phase extraction material. The preparation method includes the following steps.

In S1, 5 g of humic acid sample on sale in China is weighed and then put into a 1 L beaker; 500 mL of water is added and full stirring is performed for dispersion; the beaker is put into an ultrasonic bath for 16 min, incubation is performed at room temperature for 8 h after cleaning, and a supernatant is removed; 500 mL of water is added again, ultrasonic cleaning is performed for 16 min, incubation is performed at room temperature for 8 h, and a supernatant is removed; and the above steps are cyclically repeated for 10 times until there is no obvious light yellow in the supernatant under natural light by visual inspection. If particles in the beaker are not completely precipitated after the sample incubating at room temperature for 8 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:6:6:1; the Soxhlet extractor is placed in a water bath and heated, wherein a water bath temperature is 82° C., and the heating reflux time is 30 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h, and the refluxed liquid in the extractor remains clear.

In S3, the material in the filtration paper cylinder cleaned in the step S2 is taken out; the cleaned material is dried at a drying temperature of 100° C. for 2 h; the dried material is put into the desiccator for cooling for 1 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

Figure 4:
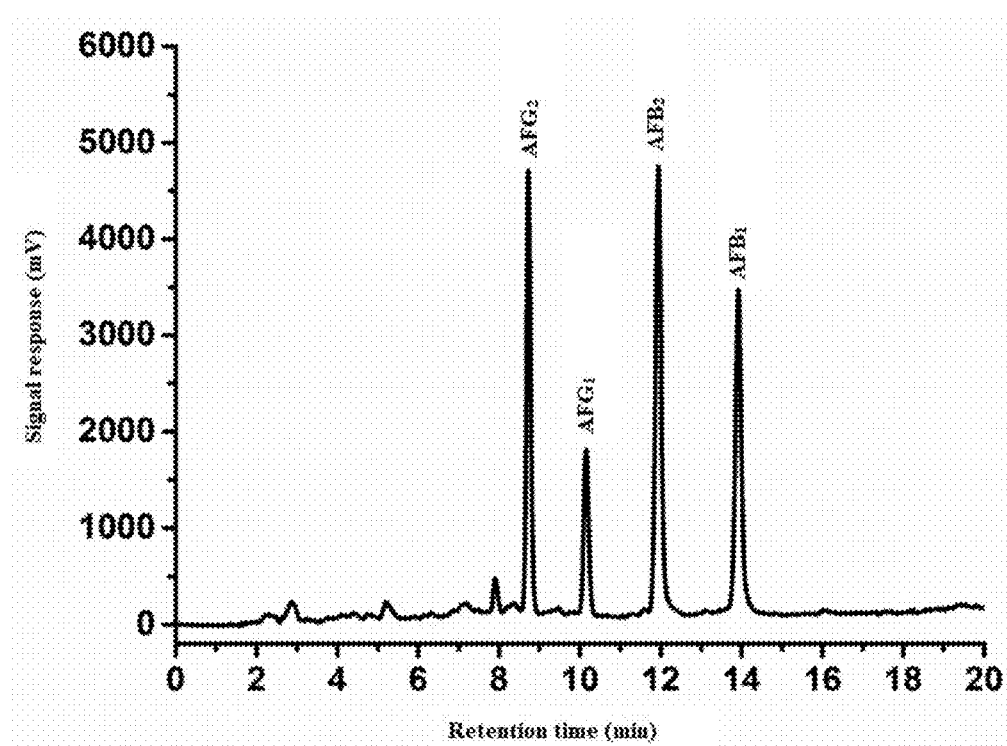

This embodiment provides a method for detecting an aflatoxin in an edible oil using the dispersive solid-phase extraction material prepared through the above preparation method. The method is particularly a sample pretreatment method and includes the following steps. 1 g of blank rapeseed oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 15 min at 11,000 r/min, and a supernatant is removed; and 5 mL of n-hexane is added again, the second shaking is performed for 30 s, the second centrifugation is performed for 5 min at 11,000 r/min, and a supernatant is removed; 4 mL of eluent is added, and shaking and centrifugation are performed, wherein the eluent includes acetonitrile and water in a volume ratio of 9:1, specifically, the shaking is performed for 1.5-2 min and the centrifugation is performed for 5 min at 9,000 r/min; all the supernatant is sucked out using a 5 mL syringe after the centrifugation ends; filtration is performed through a 0.22-μm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD. A specific LC-FLD detection chromatogram is as shown in FIG. 4.

Embodiment 6

The present application provides a preparation method of a dispersive solid-phase extraction material. The preparation method includes the following steps.

In S1, 5 g of imported humic acid sample on sale is weighed and then put into a 1 L beaker; 500 mL of water is added and full stirring is performed for dispersion; the beaker is put into an ultrasonic bath for 15 min, incubation is performed at room temperature for 6 h after cleaning, and a supernatant is removed; 500 mL of water is added again, ultrasonic cleaning is performed for 15 min, incubation is performed at room temperature for 6 h, and a supernatant is removed; and the above steps are cyclically repeated for 10 times until there is no obvious light yellow in the supernatant under natural light by visual inspection. If particles in the beaker are not completely precipitated after the sample incubating at room temperature for 8 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:6:6:1; the Soxhlet extractor is placed in a water bath and heated, wherein a water bath temperature is 82° C., and the heating reflux time is 20 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h, and the refluxed liquid in the extractor remains clear.

In S3, the material in the filtration paper cylinder cleaned in the step S2 is taken out; the cleaned material is dried at a drying temperature of 100° C. for 2 h; the dried material is put into the desiccator for cooling for 0.5 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

This embodiment provides a method for detecting an aflatoxin in an edible oil using the dispersive solid-phase extraction material prepared through the above preparation method. The method is particularly a sample pretreatment method and includes the following steps. 1 g of blank sesame oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 10 min at 9,000 r/min, and a supernatant is removed; and 5 mL of n-hexane is added again, the second shaking is performed for 30 s, the second centrifugation is performed for 5 min at 9,000 r/min, and a supernatant is removed; 4 mL of eluent is added, and shaking and centrifugation are performed, wherein the eluent includes acetonitrile and water in a volume ratio of 9:1, specifically, the shaking is performed for 1.5-2 min and the centrifugation is performed for 5 min at 9,000 r/min; all the supernatant is sucked out using a 5 mL syringe after the centrifugation ends; filtration is performed through a 0.22-μm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD.

Embodiment 7

The present application provides a preparation method of a dispersive solid-phase extraction material. The preparation method includes the following steps.

In S1, 5 g of imported humic acid sample on sale is weighed and then put into a 1 L beaker; 500 mL of water is added and full stirring is performed for dispersion; the beaker is put into an ultrasonic bath for 18 min, incubation is performed at room temperature for 6 h after cleaning, and a supernatant is removed; 500 mL of water is added again, ultrasonic cleaning is performed for 18 min, incubation is performed at room temperature for 6 h, and a supernatant is removed; and the above steps are cyclically repeated for 10 times until there is no obvious light yellow in the supernatant under natural light by visual inspection. If particles in the beaker are not completely precipitated after the sample incubating for 6 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:6:6:2; the Soxhlet extractor is placed in a water bath and heated, wherein a water bath temperature is 82° C., and the heating reflux time is 8 h, the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h and the refluxed liquid in the extractor remains clear.

In S3, the material in the filtration paper cylinder cleaned in the step S2 is taken out; the cleaned material is dried at a drying temperature of 100° C. for 2.5 h; the dried material is put into the desiccator for cooling for 1 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

This embodiment provides a method for detecting an aflatoxin in an edible oil using the dispersive solid-phase extraction material prepared through the above preparation method. The method is particularly a sample pretreatment method and includes the following steps. 1 g of blank soybean oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 2 min, the first centrifugation is performed for 20 min at 12,000 r/min, and a supernatant is removed; and 5 mL of n-hexane is added again, the second shaking is performed for 30 s, the second centrifugation is performed for 5 min at 9,000 r/min, and a supernatant is removed; 4 mL of eluent is added, and shaking and centrifugation are performed, wherein the eluent includes acetonitrile and water in a volume ratio of 9:1, specifically, the shaking is performed for 1.5-2 min and the centrifugation is performed for 5 min at 9,000 r/min; all the supernatant is sucked out using a 5 mL syringe after the centrifugation ends; filtration is performed through a 0.22-μm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD.

Embodiment 8

The present application provides a preparation method of a dispersive solid-phase extraction material. The preparation method includes the following steps.

In S1, 5 g of imported humic acid sample on sale is weighed and then put into a 1 L beaker; 500 mL of water is added and full stirring is performed for dispersion; the beaker is put into an ultrasonic bath for 15 min, incubation is performed at room temperature for 6 h after cleaning, and a supernatant is removed; 500 mL of water is added again, ultrasonic cleaning is performed for 15 min, incubation is performed at room temperature for 6 h, and a supernatant is removed; and the above steps are cyclically repeated for 10 times until there is no obvious light yellow in the supernatant under natural light by visual inspection. If particles in the beaker are not completely precipitated after the sample incubating at room temperature for 8 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:6:6:1; the Soxhlet extractor is placed in a water bath and heated, wherein a water bath temperature is 82° C., and the heating reflux time is 9 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h, and the refluxed liquid in the extractor remains clear.

In S3, the material in the filtration paper cylinder cleaned in the step S2 is taken out; the cleaned material is dried at a drying temperature of 100° C. for 2 h; the dried material is put into the desiccator for cooling for 0.5 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

This embodiment provides a method for detecting an aflatoxin in an edible oil using the dispersive solid-phase extraction material prepared through the above preparation method. The method is particularly a sample pretreatment method and includes the following steps. 1 g of blank rice bran oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 10 min at 9,000 r/min, and a supernatant is removed; and 5 mL of n-hexane is added again, the second shaking is performed for 30 s, the second centrifugation is performed for 5 min at 9,000 r/min, and a supernatant is removed; 4 mL of eluent is added, and shaking and centrifugation are performed, wherein the eluent includes acetonitrile and water in a volume ratio of 9:1, specifically, the shaking is performed for 1.5-2 min and the centrifugation is performed for 5 min at 9,000 r/min; all the supernatant is sucked out using a 5 mL syringe after the centrifugation ends; filtration is performed through a 0.22-μm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD.

Embodiment 9

The present application provides a preparation method of a dispersive solid-phase extraction material. The preparation method includes the following steps.

In S1, 5 g of imported humic acid sample on sale is weighed and then put into a 1 L beaker; 500 mL of water is added and full stirring is performed for dispersion; the beaker is put into an ultrasonic bath for 12 min, incubation is performed at room temperature for 6 h after cleaning, and a supernatant is removed; 500 mL of water is added again, ultrasonic cleaning is performed for 15 min, incubation is performed at room temperature for 6 h, and a supernatant is removed; and the above steps are cyclically repeated for 10 times until there is no obvious light yellow in the supernatant under natural light by visual inspection. If particles in the beaker are not completely precipitated after the sample incubating at room temperature for 8 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:5:6:1; the Soxhlet extractor is placed in a water bath and heated, wherein a water bath temperature is 82° C., and the heating reflux time is 12 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h, and the refluxed liquid in the extractor remains clear.

In S3, the material in the filtration paper cylinder cleaned in the step S2 is taken out; the cleaned material is dried at a drying temperature of 100° C. for 2 h; the dried material is put into the desiccator for cooling for 0.5 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

This embodiment provides a method for detecting an aflatoxin in an edible oil using the dispersive solid-phase extraction material prepared through the above preparation method. The method is particularly a sample pretreatment method and includes the following steps. 1 g of blank corn oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 10 min at 9,000 r/min, and a supernatant is removed; and 5 mL of n-hexane is added again, the second shaking is performed for 30 s, the second centrifugation is performed for 5 min at 9,000 r/min, and a supernatant is removed; 4 mL of eluent is added, and shaking and centrifugation are performed, wherein the eluent includes acetonitrile and water in a volume ratio of 9:1, specifically, the shaking is performed for 2 min and centrifugation is performed for 5 min at 9,000 r/min; all the supernatant is sucked out using a 5 mL syringe after the centrifugation ends; filtration is performed through a 0.22-μm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD.

Embodiment 10

The present application provides a preparation method of a dispersive solid-phase extraction material. The preparation method includes the following steps.

In S1, 5 g of imported humic acid sample on sale is weighed and then put into a 1 L beaker; 500 mL of water is added and full stirring is performed for dispersion; the beaker is put into an ultrasonic bath for 15 min, incubation is performed at room temperature for 7 h after cleaning, and a supernatant is removed; 500 mL of water is added again, ultrasonic cleaning is performed for 15 min, incubation is performed at room temperature for 7 h, and a supernatant is removed; and the above steps are cyclically repeated for 10 times until there is no obvious light yellow in the supernatant under natural light by visual inspection. If particles in the beaker are not completely precipitated after the sample incubating at room temperature for 8 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 7:4:7:1; the Soxhlet extractor is placed in a water bath and heated, wherein a water bath temperature is 82° C., and the heating reflux time is 15 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h and the refluxed liquid in the extractor remains clear.

In S3, the material in the filtration paper cylinder cleaned in the step S2 is taken out; the cleaned material is dried at a drying temperature of 100° C. for 2 h; the dried material is put into the desiccator for cooling for 0.5 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

This embodiment provides a method for detecting an aflatoxin in an edible oil using the dispersive solid-phase extraction material prepared through the above preparation method. The method is particularly a sample pretreatment method and includes the following steps. 1 g of blank peanut oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 10 min at 9,000 r/min, and a supernatant is removed; and 5 mL of n-hexane is added again, the second shaking is performed for 30 s, the second centrifugation is performed for 5 min at 9,000 r/min, and a supernatant is removed; 4 mL of eluent is added, and shaking and centrifugation are performed, wherein the eluent includes acetonitrile and water in a volume ratio of 9:1, specifically, the shaking is performed for 1.5-2 min and the centrifugation is performed for 5 min at 9,000 r/min; all the supernatant is sucked out using a 5 mL syringe after the centrifugation ends; filtration is performed through a 0.22-μm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD.

Embodiment 11

The present application provides a preparation method of a dispersive solid-phase extraction material. The preparation method includes the following steps.

In S1, 5 g of humic acid sample on sale in China is weighed and then put into a 1 L beaker; 500 mL of water is added and full stirring is performed for dispersion; the beaker is put into an ultrasonic bath for 15 min, incubation is performed at room temperature for 8 h after cleaning, and a supernatant is removed; 500 mL of water is added again, ultrasonic cleaning is performed for 15 min, incubation is performed at room temperature for 8 h, and a supernatant is removed; and the above steps are cyclically repeated for 10 times until there is no obvious light yellow in the supernatant under natural light by visual inspection. If particles in the beaker are not completely precipitated after the sample incubating at room temperature for 8 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:6:6:1; the Soxhlet extractor is placed in a water bath and heated, wherein a water bath temperature is 82° C., and the heating reflux time is 30 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h and the refluxed liquid in the extractor remains clear.

In S3, the material in the filtration paper cylinder cleaned in the step S2 is taken out; the cleaned material is dried at a drying temperature of 100° C. for 2 h; the dried material is put into the desiccator for cooling for 0.5 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

Figure 5:
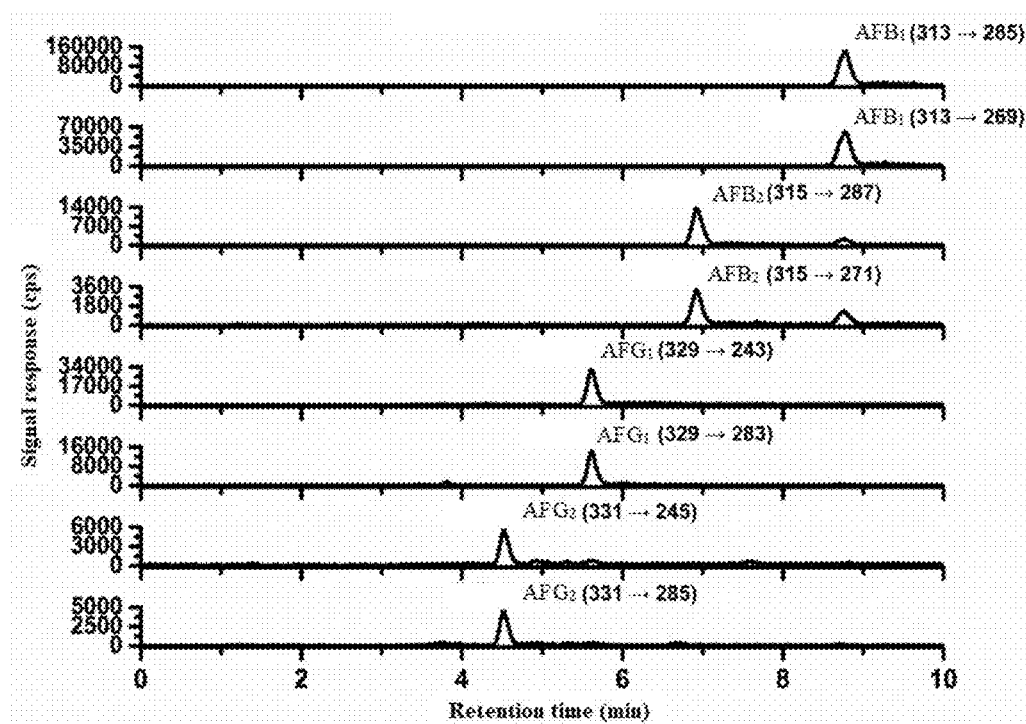

This embodiment provides a method for detecting an aflatoxin in an edible oil using the dispersive solid-phase extraction material prepared through the above preparation method. The method is particularly a sample pretreatment method and includes the following steps. 1 g of actually positive peanut oil sample on sale and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 10 min at 9,000 r/min, and a supernatant is removed; and 5 mL of n-hexane is added again, the second shaking is performed for 30 s, the second centrifugation is performed for 5 min at 9,000 r/min, and a supernatant is removed; 4 mL of eluent is added, and shaking and centrifugation are performed, wherein the eluent includes acetonitrile and water in a volume ratio of 9:1, specifically, the shaking is performed for 1.5-2 min and the centrifugation is performed for 5 min at 9,000 r/min; all the supernatant is sucked out using a 5 mL syringe after the centrifugation ends; filtration is performed through a 0.22-µm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD. A specific LC-MS detection chromatogram is as shown in FIG. 5.

Embodiment 12

The present application provides a preparation method of a dispersive solid-phase extraction material. The preparation method includes the following steps.

In S1, 5 g of imported humic acid sample on sale is weighed and then put into a 1 L beaker; 500 mL of water is added and full stirring is performed for dispersion; the beaker is put into an ultrasonic bath for 15 min, incubation is performed at room temperature for 8 h after cleaning, and a supernatant is removed; 500 mL of water is added again, ultrasonic cleaning is performed for 15 min, incubation is performed at room temperature for 8 h, and a supernatant is removed; and the above steps are cyclically repeated for 10 times until there is no obvious light yellow in the supernatant under natural light by visual inspection. If particles in the beaker are not completely precipitated after the sample incubating at room temperature for 8 h in the sample incubation process, the above steps are still cyclically repeated for 10 times for cleaning; the cleaned sample and water together are transferred into a centrifuge tube for centrifugation for 6 min at 5,000 r/min to obtain a solid precipitate; the precipitate is transferred into a 75 mL evaporating dish using acetone, the evaporating dish is heated in a water bath at 50° C., and a remaining residue is taken out after the acetone is evaporated; the residue is put into a blast drying oven at 100° C. and dried for 1 h, and then taken out; and then the residue is put into a desiccator for cooling for 20 min, the cooled residue is taken out, and the residue is ground and pulverized with a grinding rod to obtain a fine granular residue.

In S2, the residue obtained in the step S1 is put into a filtration paper cylinder; the filtration paper cylinder is put into an extraction apparatus of an Soxhlet extractor; 180 mL of cleaning liquid is added, wherein the cleaning liquid includes acetone, methanol, acetonitrile and water in a volume ratio of 6:6:6:1; the Soxhlet extractor is placed in a water bath and heated, wherein a water bath temperature is 82° C., and the heating reflux time is 20 h; the cleaning liquid evaporates and refluxes to clean the residue repeatedly until a refluxed liquid in the Soxhlet extractor is clear and colorless, and heating is stopped; and the filtration paper cylinder is taken out of the Soxhlet extractor and at the same time, it is confirmed that the extraction is stopped for 12 h and the refluxed liquid in the extractor remains clear.

In S3, the material in the filtration paper cylinder cleaned in the step S2 is taken out; the cleaned material is dried at a drying temperature of 100° C. for 2 h; the dried material is put into the desiccator for cooling for 0.5 h and then screened with a 120-mesh standard testing sieve; and a substance under the sieve is collected to obtain a dispersive solid-phase extraction material. This dispersive solid-phase extraction material is a black powdery material by visual inspection, and if there is no yellow powder in this dispersive solid-phase extraction material, this dispersive solid-phase extraction material is determined as the dispersive solid-phase extraction material. The dispersive solid-phase extraction material is sealed, dried and stored.

This embodiment provides a method for detecting an aflatoxin in an edible oil using the dispersive solid-phase extraction material prepared through the above preparation method. The method is particularly a sample pretreatment method and includes the following steps. 1 g of a blank blended oil sample quantitatively added with a known amount of aflatoxins and 50 mg of dispersive solid-phase extraction material prepared above are weighed and then placed in a 50 mL centrifuge tube; 5 mL of n-hexane is added; shaking and centrifugation are performed, wherein specifically, the shaking and the centrifugation are performed for two times: the first shaking is performed for 1.5 min, the first centrifugation is performed for 10 min at 9,000 r/min, and a supernatant is removed; and 5 mL of n-hexane is added again, the second shaking is performed for 30 s, the second centrifugation is performed for 5 min at 9,000 r/min, and a supernatant is removed; 4 mL of eluent is added, and shaking and centrifugation are performed, wherein the eluent includes acetonitrile and water in a volume ratio of 9:1, specifically, the shaking is performed for 1.5-2 min and the centrifugation is performed for 5 min at 9,000 r/min; all the supernatant is sucked out using a 5 mL syringe after the centrifugation ends; filtration is performed through a 0.22-µm microporous membrane, and the filtered material is transferred into a new centrifuge tube and dried at a temperature less than 40° C. to obtain a sample to be measured, a solution including methanol and water which are mixed in a volume ratio of 1:1 is added to the sample to be measured to redissolve the sample, and the solution is analyzed through LC-MS or LC-FLD.

Specifically, by performing LC-MS detection on Embodiments 1-10, matrix effect values and recovery rates of blank spiked samples which are treated by the dispersive solid-phase extraction material prepared by this method prior to detection. Influences of the sample matrixes treated by the dispersive solid-phase extraction material on detection results are determined and shown as the matrix effect values. When the matrix effect value is greater than 100%, positive interference will occur, resulting in a positive deviation in the detection result, and at the same time, the larger the value is, the larger the interference is. When the matrix effect value is less than 100%, negative interference will occur, resulting in a negative deviation in the detection result, and at the same time, the smaller the value is, the larger the interference is and the greater the deviation in the detection result is. When the matrix effect value is equal to 100%, no interference will occur. Moreover, the extraction efficiencies of aflatoxins by the dispersive solid-phase extraction material are determined based on the recovery rates. When the recovery rate is equal to 100%, it means that all the aflatoxins are extracted out, and the closer the recovery rate is to 100%, the better the extraction effect is and the more accurate the detection result is. Specific detection results are shown in Table 1 and Table 2 below.

TABLE 1

| Embodiment | Matrix Effect (%) | | | |
|---|---|---|---|---|
| | $AFB_1$ | $AFB_2$ | $AFG_1$ | $AFB_2$ |
| Embodiment 1 | 109.4 ± 1.8 | 92.0 ± 0.6 | 93.8 ± 6.5 | 93.7 ± 9.4 |
| Embodiment 2 | 106.2 ± 0.5 | 96.8 ± 7.2 | 101.7 ± 10.3 | 112.9 ± 1.4 |
| Embodiment 3 | 105.9 ± 0.4 | 92.5 ± 0.1 | 107.6 ± 2.2 | 100.9 ± 10.6 |
| Embodiment 4 | 99.2 ± 1.8 | 100.9 ± 9.8 | 105.3 ± 10.0 | 110.9 ± 3.4 |
| Embodiment 5 | 105.6 ± 2.5 | 101.4 ± 2.5 | 104.3 ± 9.9 | 108.1 ± 2.6 |
| Embodiment 6 | 101.4 ± 2.5 | 93.1 ± 0.4 | 105.6 ± 2.2 | 93.8 ± 1.1 |
| Embodiment 7 | 93.6 ± 0.4 | 97.5 ± 0.9 | 107.6 ± 2.2 | 96.2 ± 9.5 |
| Embodiment 8 | 104.4 ± 6.4 | 106.8 ± 9.2 | 98.7 ± 2.1 | 103.3 ± 8.1 |
| Embodiment 9 | 94.2 ± 0.6 | 90.3 ± 3.3 | 101.2 ± 4.5 | 99.1 ± 7.6 |
| Embodiment 10 | 97.9 ± 7.1 | 89.3 ± 9.3 | 93.2 ± 2.7 | 98.6 ± 9.5 |

TABLE 2

| Embodiment | Recovery Rate (%) | | | |
|---|---|---|---|---|
| | $AFB_1$ | $AFB_2$ | $AFG_1$ | $AFB_2$ |
| Embodiment 1 | 87.5 ± 3.2 | 89.6 ± 1.3 | 92.0 ± 0.3 | 91.8 ± 1.0 |
| Embodiment 2 | 87.1 ± 0.1 | 89.2 ± 0.0 | 91.4 ± 0.0 | 92.6 ± 0.4 |
| Embodiment 3 | 81.3 ± 2.1 | 83.4 ± 0.9 | 87.0 ± 0.6 | 86.3 ± 0.6 |
| Embodiment 4 | 84.7 ± 1.3 | 86.7 ± 1.8 | 88.6 ± 1.0 | 90.8 ± 1.4 |
| Embodiment 5 | 84.0 ± 4.0 | 82.1 ± 1.8 | 88.3 ± 0.3 | 85.1 ± 0.8 |
| Embodiment 6 | 85.7 ± 5.0 | 83.8 ± 2.9 | 98.0 ± 3.1 | 93.7 ± 4.1 |
| Embodiment 7 | 94.6 ± 0.8 | 95.6 ± 0.7 | 104.8 ± 0.2 | 102.3 ± 0.1 |
| Embodiment 8 | 88.9 ± 0.5 | 86.2 ± 0.1 | 94.0 ± 2.9 | 91.0 ± 0.1 |
| Embodiment 9 | 97.0 ± 1.5 | 94.6 ± 0.9 | 106.2 ± 1.0 | 102.6 ± 1.7 |
| Embodiment 10 | 87.5 ± 0.2 | 83.3 ± 1.6 | 91.1 ± 1.0 | 87.6 ± 0.5 |

In addition, the dispersive solid-phase extraction materials prepared by using the domestic humic acid on sale and those prepared by using the imported humic acid on sale are used in Embodiment 1 and Embodiment 12 respectively. The comparison of three groups of dispersive solid-phase materials which are prepared from the domestic humic acids on sale and three groups of dispersive solid-phase materials which are prepared from the imported humic acids on sale through parallel tests shows the basically identical effect. Therefore, the dispersive solid-phase extraction material preparation method is suitable for humic acids on sale at home and abroad. Within an allowable error range, the humic acid used in the present invention is a humic acid containing black humic acid. Only this kind of humic acid can be applied to the present invention and make the present invention achieve the same technical effect. However, a humic acid mainly containing fulvic acid is not suitable for the present invention and cannot achieve the technical effect described in the present invention. Specific comparative results are as shown in Table 3 below.

TABLE 3

| Brand of Humic Acid | Recovery Rate (%) | | | |
|---|---|---|---|---|
| | $AFB_1$ | $AFB_2$ | $AFG_1$ | $AFB_2$ |
| Domestic Humic Acid 1 | 84.1 ± 1.1 | 81.5 ± 0.2 | 103.0 ± 2.1 | 95.9 ± 2.0 |
| Domestic Humic Acid 2 | 91.8 ± 1.0 | 92.0 ± 0.3 | 89.6 ± 1.3 | 87.5 ± 3.2 |
| Domestic Humic Acid 3 | 85.6 ± 2.5 | 82.9 ± 1.1 | 84.1 ± 3.0 | 82.7 ± 1.2 |
| Imported Humic Acid 1 | 84.5 ± 0.7 | 93.7 ± 0.5 | 94.7 ± 0.8 | 95.2 ± 1.9 |
| Imported Humic Acid 2 | 87.9 ± 0.3 | 93.8 ± 0.2 | 96.4 ± 0.2 | 100.1 ± 0.9 |
| Imported Humic Acid 3 | 90.6 ± 0.7 | 89.0 ± 0.6 | 90.6 ± 1.0 | 94.4 ± 1.3 |

In addition, the comparison of detection data of Embodiment 1 and detection data of an existing standard aflatoxin detection method, i.e., the immunoaffinity column (IAC) shows that the dispersive solid-phase extraction materials prepared through this preparation method and the sample pretreatment method have the same detection effect as the existing immunoaffinity column Thus, this pretreatment method satisfies requirements of detection standards. Specific data results are as shown in Table 4 below.

TABLE 4

| Blind Sample Testing | IAC | | Method According to the Present Invention | |
|---|---|---|---|---|
| Aflatoxin | Theoretical Value (µg/kg) | Measured value (µg/kg) | Error (%) | Measured value (µg/kg) | Error (%) |
| $AFB_1$ | 15.9 | 16.8 | 5.7 | 14.5 | −8.8 |
| $AFB_2$ | 2.41 | 2.38 | −1.2 | 2.20 | −8.7 |
| $AFG_1$ | 5.00 | 5.13 | 2.6 | 4.96 | −0.9 |
| $AFG_2$ | 2.45 | 2.56 | 4.5 | 2.48 | 1.2 |

Moreover, this method has simple detection steps and a low cost, and the detection cost of each sample of this method is RMB 10-30 yuan compared to RMB 200-500 yuan per sample of the IAC. Therefore, this method facilitates low-cost detection of the aflatoxins in the edible oils.

In addition, in the above embodiments, when the dispersive solid-phase extraction material is prepared, if the refluxed liquid still fails to show an obvious clear state after the filtration paper cylinder filled with the residue is cleaned via refluxing for 20 h in the Soxhlet extractor, for improving the cleaning efficiency, the filtration paper cylinder filled with the residue is taken out of the extraction apparatus of the Soxhlet extractor, the residue is taken out, air-dried naturally, ground, pulverized and dispersed again and then placed in a new filtration paper cylinder. The new filtration paper cylinder is put into another clean Soxhlet extractor, 180 mL of cleaning liquid is added again for cleaning by refluxing for 8-12 h until the refluxed liquid is clear and colorless, and then the filtration paper cylinder is taken out of the Soxhlet extractor.

Soxhlet extraction and dispersive solid-phase extraction in the technical approaches used in the above embodiments are conventional approaches known to those skilled in the art. Specifically, a mass spectrometer used in LC-MS analysis is Triple Quad 5500 from SCIEX, United States, using an electrospray ionization source. A liquid chromatograph is Shimadzu LC-30 UFLC, Japan, which is equipped with an LC-30AD binary high-pressure gradient pump, an SIL-30AC automatic sampler, a CTO-30A constant-temperature column oven, and a DGU-20A5R degasser. A C18 reversed-phase chromatography column (100 mm*3.0 mm, 2.6 µm) is used for compound separation with a column temperature controlled at 40° C. A mobile phase includes water and methanol. The chromatographic flow velocity is 0.3 mL/min, and the mobile phase adopts isocratic elution of 42% mobile phase B. A liquid chromatograph used in LC-FLD analysis is Shimadzu LC-20 HPLC, Japan, which is equipped with an LC-20AT binary high-pressure gradient pump, an SIL-20A automatic sampler, a CTO-20A3R constant-temperature column oven, a DGU-20A3 degasser and an RF-20A fluorescence detector. A C18 reversed-phase chromatography column (150 mm*4.6 mm, 5 μm) is used for compound separation with a column temperature controlled at 40° C. A mobile phase includes water and methanol. The chromatographic flow velocity is 0.8 mL/min, and the mobile phase adopts gradient elution. Specifically, 45% phase B is maintained for 4 min, and then phase B rises to 53% within 10 min.

Samples are treated with dispersive solid-phase extraction material prepared through the preparation method according to the present application prior to detection. Detection is performed for Embodiment 1, Embodiment 5 and Embodiment 11. In Embodiment 1, the blank blended oil sample quantitatively added with aflatoxins is analyzed, the amounts of $AFB_1$, $AFB_2$, $AFG_1$ and $AFG_2$ are known and thus an extraction effect of this dispersive solid-phase extraction material can be validated (as shown in FIG. 3 in detail). In Embodiment 5, the blank rapeseed oil sample quantitatively added with aflatoxins is analyzed, the amounts of $AFB_1$, $AFB_2$, $AFG_1$ and $AFG_2$ in the aflatoxin are known and thus an extraction effect of this dispersive solid-phase extraction material can be validated (as shown in FIG. 4 in detail). In Embodiment 11, the positive peanut oil sample on sale is measured and specific detection results for individual AF are as shown in FIG. 5 which includes chromatograms for $AFB_1$, $AFB_2$, $AFG_1$ and $AFG_2$. In this figure, chromatographic peaks correspond to $AFB_1$, $AFB_2$, $AFG_1$ and $AFG_2$ respectively. The humic acid contains water-soluble fulvic acid, ulmic acid soluble in acetone and ethanol, and black humic acid which is neither soluble in water nor acetone and ethanol. Only black humic acid is suitable as the dispersive solid phase extraction material to extract and purify the AFs in edible oils. The material cleaning method provided by the present invention can fully remove fulvic acid and ulmic acid components, and effectively retain the black humic acid in the humic acid. Therefore, the dispersive solid-phase extraction material prepared through the preparation method can extract and detect the AFs in the edible oils with accurate detection results and good repeatability.

The above descriptions are only preferred embodiments of the present invention, and are not intended to limit the present invention. Any modifications, equivalent replacements, improvements and the like made within the spirit and principles of the present invention should be included within the scope of protection of the present invention.

The invention claimed is:

1. A preparation method of a dispersive solid-phase extraction material, comprising the following steps:
    S1. weighing a humic acid containing black humic acid, performing ultrasonic washing for 12-18 min, performing centrifugation after washing to obtain a solid precipitate, resuspending the solid precipitate in acetone, and performing heating for evaporation until the acetone is completely evaporated to obtain a residue;
    S2. placing the residue obtained in the step S1 in a Soxhlet extractor, adding 180 mL of cleaning liquid, wherein the liquid for cleaning comprises acetone, methanol, acetonitrile and water in a volume ratio of 6-8:4-6:6-8:1-2, performing heating reflux for cleaning until the refluxed liquid is clear and colorless, and stopping heating; and
    S3. taking out the material cleaned in the step S2, drying the material at 100° C. for 1.5-2.5 h, cooling the dried material for 0.5-1 h, then screening the cooled material through a 120-mesh sieve, and obtaining a substance under the sieve, i.e., the dispersive solid-phase extraction material.

2. The preparation method according to claim 1, wherein in the step S1, after ultrasonic washing, standing is performed for 6-10 h, a supernatant is removed, the operation of ultrasonic washing and standing is cyclically repeated for 10 times, and then centrifugation is performed to obtain the solid precipitate.

3. The preparation method according to claim 1, wherein heating the Soxhlet extractor in the step S2 comprises heating the Soxhlet extractor in a water bath, wherein a water bath temperature is 70-90° C., and the heating time is 8-30 h.

4. The preparation method according to claim 3, wherein in the step S2, the residue which is subjected to heating reflux for 20 h is taken out, the residue is air-dried naturally, ground, and then placed in another Soxhlet extractor, then 180 mL of cleaning liquid is added, heating is performed again for cleaning for 8-12 h until the refluxed liquid is clear and colorless, and heating is stopped.

5. A method for detecting an aflatoxin in an edible oil, comprising sample pretreatment and being characterized by comprising: weighing and mixing 1 g of edible oil sample and 50 mg of dispersive solid-phase extraction material prepared by the preparation method of claim 1, adding 5 mL of n-hexane, performing shaking and centrifugation and removing a supernatant; and then adding 4 mL of eluent, performing shaking and centrifugation, wherein the liquid for cleaning comprises acetonitrile and water in a volume ratio of 9:1, taking a supernatant, drying the supernatant to obtain a sample to be measured, dissolving the sample to be measured and measuring the dissolved sample.

6. The method for detecting the aflatoxin in the edible oil according to claim 5, wherein the operation of adding the n-hexane, performing the shaking and centrifugation and removing the supernatant specifically is specifically performed for two times, wherein in the first operation comprises: adding 5 mL of n-hexane, performing shaking for 1.5-2 min, then performing centrifugation for 10-20 min at 9,000-12,000 r/min, and removing the supernatant; the second operation comprises: adding 5 mL of n-hexane, performing shaking for 20-40 s, then performing centrifugation for 5 min at 9,000-12,000 r/min, and removing the supernatant; and in the operation of adding the eluent and performing the shaking and centrifugation, the shaking is performed for 1.5-2 min and the centrifugation is then performed for 5 min at 9,000-12,000 r/min.

* * * * *